United States Patent
Herr et al.

(10) Patent No.: US 8,075,633 B2
(45) Date of Patent: Dec. 13, 2011

(54) ACTIVE ANKLE FOOT ORTHOSIS

(75) Inventors: Hugh Herr, Somerville, MA (US);
Joaquin Blaya, Santiago (CL); Gill A. Pratt, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 1499 days.

(21) Appl. No.: 10/671,329

(22) Filed: Sep. 25, 2003

(65) Prior Publication Data

US 2005/0070834 A1    Mar. 31, 2005

(51) Int. Cl.
*A61F 2/66*    (2006.01)

(52) U.S. Cl. ........................................................ 623/47

(58) Field of Classification Search ............... 607/48, 607/49, 108, 111, 144; 623/24, 27, 47, 50; 602/28
See application file for complete search history.

(56) References Cited

U.S. PATENT DOCUMENTS

| | | | |
|---|---|---|---|
| 4,569,352 A * | 2/1986 | Petrofsky et al. | 607/49 |
| 4,964,402 A * | 10/1990 | Grim et al. | 602/2 |
| 5,112,296 A * | 5/1992 | Beard et al. | 602/28 |
| RE34,661 E * | 7/1994 | Grim | 602/27 |
| 5,476,441 A * | 12/1995 | Durfee et al. | 602/23 |
| 5,556,422 A * | 9/1996 | Powell et al. | 607/48 |
| 5,643,332 A * | 7/1997 | Stein | 607/49 |
| 5,662,693 A * | 9/1997 | Johnson et al. | 607/49 |
| 5,748,845 A * | 5/1998 | Labun et al. | 706/10 |
| 5,898,948 A * | 5/1999 | Kelly et al. | 2/240 |
| 5,932,230 A * | 8/1999 | DeGrate | 424/401 |
| 5,980,435 A * | 11/1999 | Joutras et al. | 482/114 |
| 6,056,712 A * | 5/2000 | Grim | 602/27 |
| 6,267,742 B1 * | 7/2001 | Krivosha et al. | 602/28 |
| 6,443,993 B1 * | 9/2002 | Koniuk | 623/24 |
| 6,456,884 B1 * | 9/2002 | Kenney | 607/48 |
| 6,507,757 B1 * | 1/2003 | Swain et al. | 607/49 |
| 6,517,503 B1 * | 2/2003 | Naft et al. | 602/16 |
| 6,610,101 B2 * | 8/2003 | Herr et al. | 623/24 |
| 6,752,774 B2 * | 6/2004 | Townsend et al. | 602/16 |
| 6,764,520 B2 * | 7/2004 | Deffenbaugh et al. | 623/24 |
| 6,966,882 B2 * | 11/2005 | Horst | 601/5 |
| 7,641,700 B2 * | 1/2010 | Yasui | 623/40 |
| 7,736,394 B2 * | 6/2010 | Bedard et al. | 623/24 |
| 7,867,284 B2 * | 1/2011 | Bedard | 623/24 |
| 2001/0029400 A1 * | 10/2001 | Deffenbaugh et al. | 623/24 |

(Continued)

OTHER PUBLICATIONS

Blaya, J. A., and Herr, H., "Adaptive Control of a Variable-Impedance Ankle-Foot Orthosis to Assist Drop Foot Gait.".

(Continued)

*Primary Examiner* — Niketa Patel
*Assistant Examiner* — Hiba El-Kaissi
(74) *Attorney, Agent, or Firm* — Hamilton, Brook, Smith & Reynolds, P.C.

(57) ABSTRACT

An Active Ankle Foot Orthosis (AAFO) is provided where the impedance of an orthotic joint is modulated throughout the walking cycle to treat ankle foot gait pathology, such as drop foot gait. During controlled plantar flexion, a biomimetic torsional spring control is applied where orthotic joint stiffness is actively adjusted to minimize forefoot collisions with the ground. Throughout late stance, joint impedance is minimized so as not to impede powered plantar flexion movements, and during the swing phase, a torsional spring-damper (PD) control lifts the foot to provide toe clearance. To assess the clinical effects of variable-impedance control, kinetic and kinematic gait data were collected on two drop foot participants wearing the AAFO. It has been found that actively adjusting joint impedance reduces the occurrence of slap foot, allows greater powered plantar flexion, and provides for less kinematic difference during swing when compared to normals.

36 Claims, 7 Drawing Sheets

U.S. PATENT DOCUMENTS

| | | | |
|---|---|---|---|
| 2002/0052663 A1* | 5/2002 | Herr et al. | 623/24 |
| 2003/0093021 A1* | 5/2003 | Goffer | 602/23 |
| 2003/0139783 A1* | 7/2003 | Kilgore et al. | 607/49 |
| 2003/0195439 A1* | 10/2003 | Caselnova | 601/15 |
| 2004/0054423 A1* | 3/2004 | Martin | 623/25 |
| 2004/0088025 A1* | 5/2004 | Gesotti | 607/49 |
| 2004/0181118 A1* | 9/2004 | Kochamba | 600/37 |
| 2005/0049652 A1* | 3/2005 | Tong | 607/48 |
| 2005/0059908 A1* | 3/2005 | Bogert | 601/5 |
| 2006/0004307 A1* | 1/2006 | Horst | 601/5 |
| 2006/0094989 A1* | 5/2006 | Scott et al. | 601/5 |

OTHER PUBLICATIONS

Blaya, J. A., et al., "Active Ankle Foot Orthoses (AAFO)," http://www.ai.mit.edu. Artificial Intelligence Laboratory, Massachusetts Institute of Technology, Cambridge, Massachusetts.

Drake, C., "Foot & Ankle Splints or Orthoses," HemiHelp Information Sheet, London, United Kingdom.

Blaya, J. A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003).

Hogan, N., "Impedance Control: An Approach to Manipulation," pp. 304-313, (Jun. 1984).

Hogan, N., "Impedance Control: An Approach to Manipulation: Part II—Implementation," *Journal of Dynamic Systems, Measurement, and Control*, 107:8-16, (1985).

Hogan, N., "Impedance Control: An Approach to Manipulation: Part III—Applications," *Journal of Dynamics Systems, Measurement, and Control*, 107: 17-24, (1985).

* cited by examiner

ACTIVE ANKLE FOOT ORTHOSIS

BACKGROUND OF THE INVENTION

Individuals may suffer from a variety of ankle foot gait pathologies, such as muscle weakness in the anterior and/or posterior compartments of the leg, which severely inhibit locomotory function. For example, drop foot gait is the inability of an individual to lift or dorsiflex their foot because of reduced or no muscular activity, typically in the anterior compartment of the leg around their ankle. The major causes of drop foot include stroke, cerebral palsy, multiple sclerosis, and neurological trauma from accident or surgical complication. The two major complications of drop foot are slapping of the foot after heel strike (foot slap) and dragging of the toe during swing (toe drag). At heel strike, the foot generally falls uncontrolled to the ground, producing a distinctive slapping noise (foot slap). During mid-swing, toe drag prevents proper limb advancement and increases the risk of tripping.

A conventional approach to the treatment of drop foot gait is a mechanical brace called an Ankle Foot Orthosis (AFO), which has increased in popularity over the last several years. Although AFO's offer some biomechanical benefits, disadvantages still remain. For example, AFO's do not improve gait velocity or stride length in children with cerebral palsy. Further, although a constant stiffness AFO is able to provide safe toe clearance in drop foot patients, the device does not reduce the occurrence of slap foot at all walking speeds.

SUMMARY OF THE INVENTION

Increasingly, robotic technology is employed in the treatment of individuals suffering from physical disability, either for the advancement of therapy tools or permanent assistive devices. Initial research has focused primarily on devices that provide therapy to the arms of stroke patients. However, lower extremity robotic devices have recently been developed. When used for permanent assistance, adaptive orthoses enables disabled persons to walk with greater ease and less kinematic difference when compared to normals. Active leg prostheses also show promise. Preliminary studies report that the Otto Bock C-Leg, a microprocessor-controlled artificial knee, provides amputees with an increased independence compared with passive knee prostheses.

In one embodiment, a variable-impedance Active Ankle-Foot Orthosis (AAFO) is provided to treat ankle foot gait pathologies, such as drop foot gait.

Another embodiment for the treatment of ankle foot gait pathologies, such as drop foot gait, includes functional electrical stimulation (FES). Short bursts of electrical pulses can be applied to elicit muscle contractions. FES can be used as a permanent assistance device, and the technology can be customized to the individual using trial-and-error methods and qualitative measurements.

Neither AFOs nor conventional FES systems adapt to the gait of the user, adapt to step-to-step changes in gait pattern due to speed or terrain, or adapt to long-term gait changes due to changes in muscle function. In one embodiment, a computer-controlled Active Ankle Foot Orthosis (AAFO) is provided where joint impedance is varied in response to walking phase and step-to-step gait variations. The AAFO includes an actuator, such as a force-controllable Series Elastic Actuator (SEA) capable of controlling orthotic joint stiffness and damping for plantar and dorsiflexion ankle rotations.

A variable-impedance orthosis has certain clinical benefits for the treatment of drop foot gait compared to both unassisted gait and conventional AFO's that include constant impedance joint behaviors. For example, the major complications of drop foot gait, namely foot slap and toe drag, can be reduced by actively controlling orthotic joint impedance in response to walking phase and step-to-step gait variations. Recent investigations have shown that for the healthy ankle-foot complex, ankle function during controlled plantar flexion closely resembles a linear torsional spring where ankle moment is proportional to ankle position. Thus, by adjusting the stiffness of a virtual linear torsional spring acting about the orthotic joint, forefoot collisions can be minimized and the slap foot complication alleviated, not only at a single speed but at every forward walking speed. Furthermore, during swing, a spring-damper (PD) control can be applied to the orthotic joint, with gains that vary with gait speed, to dorsiflex the ankle through a greater angular range to provide sufficient clearance at variable walking speeds. For individuals suffering from unilateral drop foot gait, changing orthotic joint impedance results in a more symmetric gait between affected and unaffected legs.

BRIEF DESCRIPTION OF THE DRAWINGS

The foregoing and other objects, features and advantages of the invention will be apparent from the following more particular description of various embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of various embodiments of the invention follows.

Figure 1:
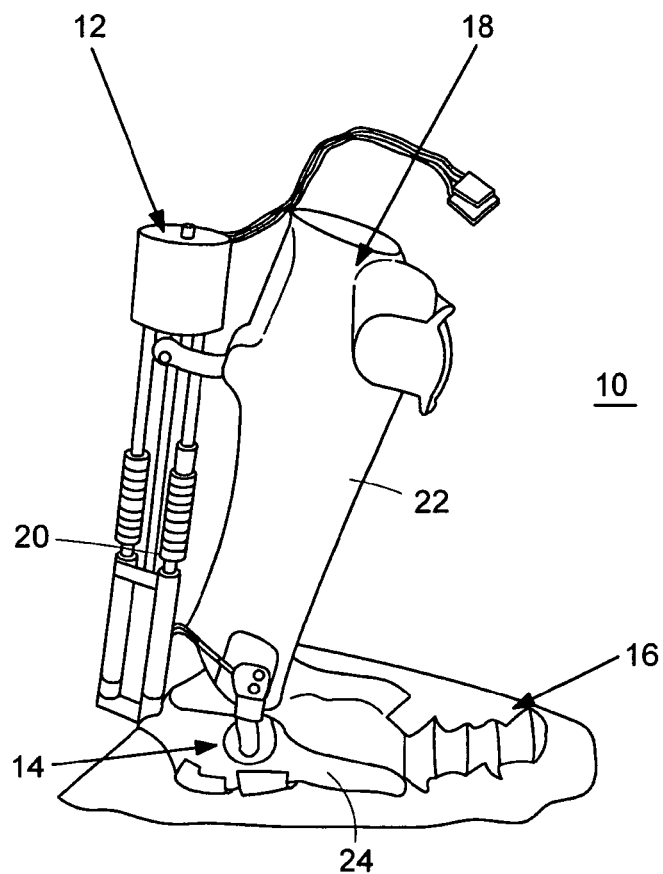
FIG. 1 is a side view of an embodiment of an Active Foot Orthosis (AAFO).

FIG. 1 illustrates an embodiment of an AAFO 10, an actuator 12, and sensors 14, 16 attached to a conventional AFO 18. In one embodiment, the AAFO 10 has a total weight of about 2.6 kg, excluding the weight of an off-board power supply. In a particular embodiment, the actuator 12 includes a Series Elastic Actuator (SEA), previously developed for legged robots, for controlling the impedance of the orthotic ankle joint for sagittal plane rotations. The SEA 12 can include a brushless DC motor in series with a spring. The SEA 12 provides force control by controlling the extent to which the series spring 20 is compressed. The deflection of the spring 20 can be measured by a linear potentiometer sampled at 1000 Hz and passed through a first order filter with a cutoff frequency equal to 50 Hz. The signal can be numerically differentiated and passed through another first order filter with a cutoff frequency of 8 Hz. The deflection of the series spring 20 can be controlled using a proportional-derivative (PD) controller.

Some advantages of the SEA 12 are that it has low impedance, the motor is isolated from shock loads, and the effects of backlash, torque ripple, and friction are filtered by the spring 20. A further advantage is that the SEA 12 exhibits stable behavior while in contact with most environments, even when in parallel with a human limb. In particular embodiments, the SEA 12 allows for the implementation of any virtual, torsion mechanical element about the ankle.

In a particular embodiment, the conventional AFO 18 includes a standard polypropylene AFO with a metallic hinge, such as a Scotty© ankle joint. This joint allows free motion in the sagittal plane (plantar and dorsiflexion) but is rigid for inversion/eversion movements. The AFO 18 can be modified by molding two recesses—one at the heel and the other at mid-calf. Several holes can be drilled in these recesses to attach the SEA 12.

In a particular embodiment, an ankle angle sensor 14 includes a Bourns 6637S-1-502 5 kΩ rotary potentiometer to determine the angle between a shank or leg portion 22, which is attachable to a person's foot, and the foot 24. The angle sensory signal can be sampled at 1000 Hz and passed through a first order low pass filter with a cutoff frequency of 50 Hz. The ankle velocity can be found by differentiating the pot signal and then passing it through a second order Butterworth filter with a cutoff frequency of 8 Hz. In another embodiment, the position of the orthotic ankle joint can be measured with a rotary encoder placed on the SEA 12. Such a sensor can measure motor position directly and orthotic position indirectly.

In other embodiments, Ground Reaction Force (GRF) sensors 16 can be used to measure forces on the foot 24. In a particular embodiment, an Ultraflex system can be used. In one embodiment, six capacitive force transducers, 25 mm square and 3 mm thick, can be placed on the bottom or foot 24 of the AFO 18, two sensors beneath the heel and four beneath the forefoot region. In particular embodiments, each sensor 16 can detect up to 1000 N, and can have a resolution of 2.5, and a scanning frequency of 125 Hz. The signal from each sensor 16 can be passed through a first-order filter with a cut-off frequency equal to 5 Hz. A single foot switch, model MA-153, can be placed in the heel of a shoe worn with the orthosis to detect heel strike approximately 30 ms earlier than the Ultraflex force sensors.

Ankle biomechanics for level ground walking on smooth surfaces can be described using four distinct walking phases. In this description, only sagittal rotations are described, that is to say, dorsi and plantarflexion and not inversion-eversion movements.

Beginning with heel strike, the stance ankle begins to plantarflex slightly. This flexion, called controlled plantarflexion, allows for a smooth heel-strike to forefoot-strike transition. Recent investigations show that the torque versus angle data are spring-like with ankle torque increasing linearly with ankle position. Although a normal, healthy ankle behaves as a passive mechanical linear spring within a contact phase, the stiffness of that linear spring is continually modulated by the central nervous system from step to step. It is believed that the body adjusts ankle spring stiffness to achieve a fixed energy absorption and release at each walking speed. Data also show that energy absorption and release increases with increasing walking speed, necessitating an increase in ankle stiffness with walking speed (when the heel-strike angle remains invariant to speed variations).

After maximum plantarflexion is reached in the stance ankle, the joint begins to dorsiflex. In this particular walking phase, called controlled dorsiflexion, the ankle also is spring-like but is distinctly nonlinear; here, ankle stiffness increases with increasing ankle dorsiflexion to gradually slow tibia progression.

During late stance, the ankle begins to power plantarflex to drive kinetic energy into the lower limb in preparation for the swing phase. For moderate to fast walking speeds, about 10-20 Joules of ankle work are performed. That energy is above and beyond the spring energies stored and released from early to late stance.

As the hip is flexed, and the knee has reached a certain angle in knee break, the leg leaves the ground and the knee continues to flex. Throughout the swing phase, the swing foot continues to rotate to cancel the angular momentum of the adjacent stance foot such that the net angular momentum contribution about the body's center of mass is zero.

Figure 2:
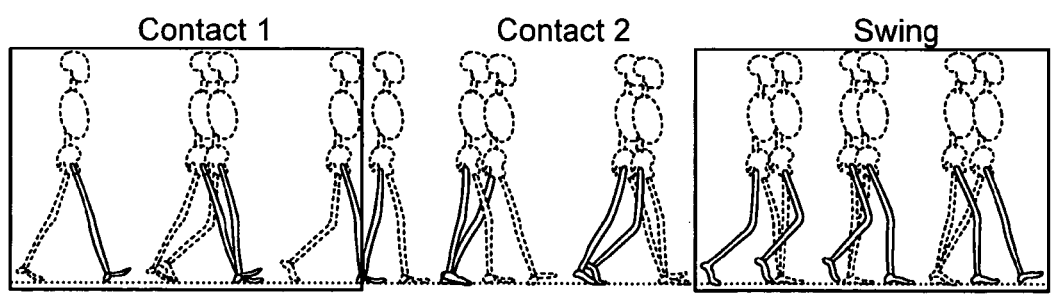
FIG. 2 illustrates individual states for a finite machine.

A finite state machine can be implemented to address each complication of an ankle foot gait pathology, such as drop foot gait. Three states were used, each with a specific control objective (FIG. 2). Contact 1 spans the first half of ground contact from heel strike to the middle of mid-stance when the tibia first becomes perpendicular with the foot. Contact 2 spans the second half of ground contact, beginning when the tibia first becomes perpendicular with the foot and ending at toe-off when the leg first loses contact with the ground. Finally, the Swing state spans the entire swing phase, from toe-off to heel strike.

Figure 3:
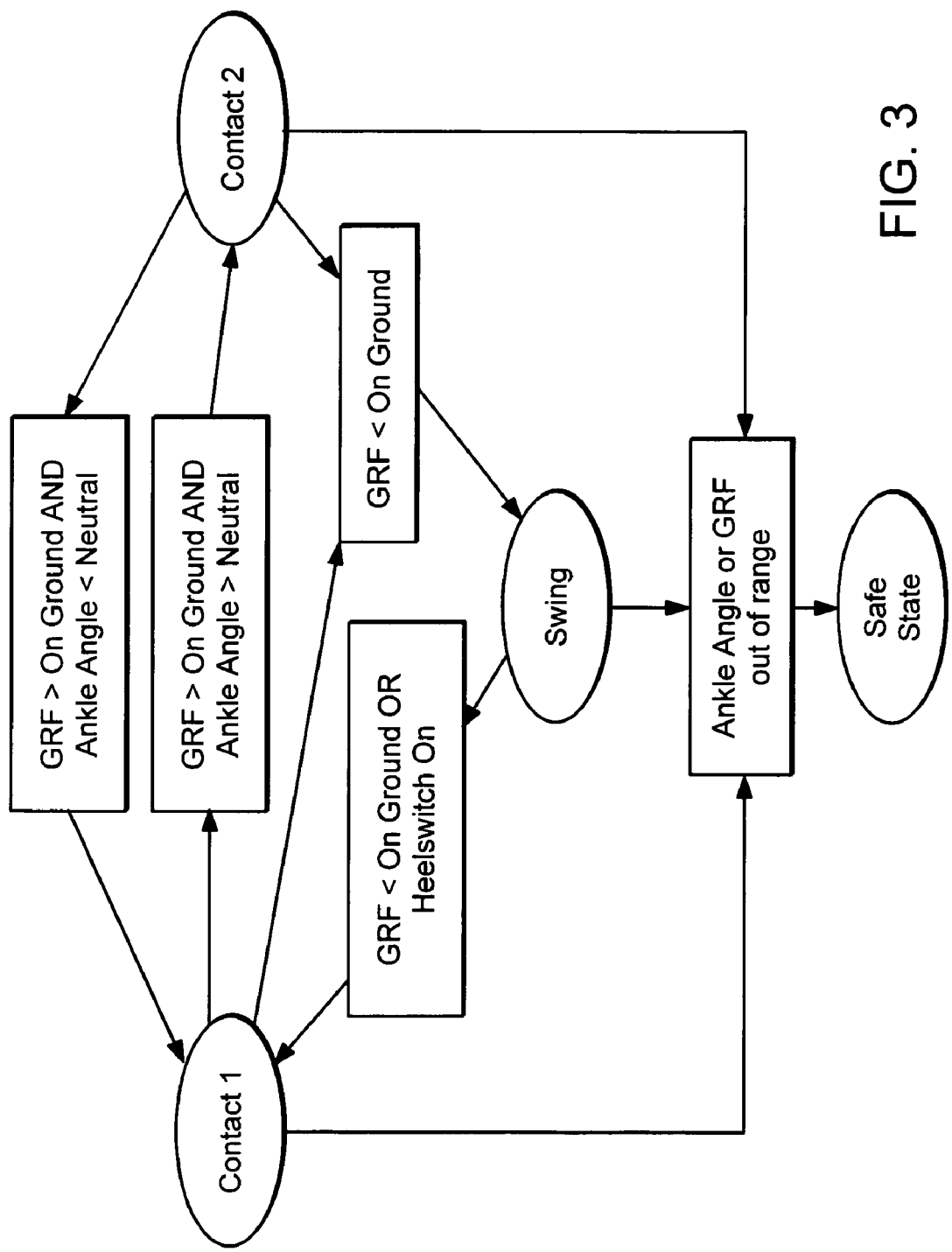
FIG. 3 illustrates triggers for the finite machine of FIG. 2.

In a Contact 1 state, from heel strike to midstance, the objective of the controller is to prevent foot slap. During a Contact 2 state, from midstance to toe-off, the controller minimizes the impedance of the brace so as not to impede power plantar flexion movements. Finally, in a Swing state, spanning the entire swing phase, the user's foot is lifted to prevent toe drag. A Safe State can be used to shut off the device when any unexpected circumstances occur. The triggers or transitional parameters for the finite state machine are shown in FIG. 3.

For a gait cycle in accordance with one embodiment, Contact 1 begins when the foot switch within the heel was compressed. In this embodiment, the transition into Contact 2 occurred when the Ground Reaction Force (GRF), equal to the sum of all six force transducers, was greater than On Ground, equal to about 60 N, and when the ankle was in dorsiflexion. The ankle was considered to be in dorsiflexion when the angle between the tibia and foot was less than 90°. In this embodiment, On Ground was set to about 60 N because this particular value reliably discerned ground contact from noise during swing. Contact 2 ended when the GRF was less than On Ground. In fact, the transition into Swing always occurred when the GRF was less than On Ground. The controller transitioned to the Safe State when any of the force or angle sensory signals went beyond a specified normal operating range. In this embodiment, the range for each force sensor was about 1000 N, the maximum force that any one sensor should measure in walking for a 90 kg person. The acceptable range for the angle sensor was about ±45 degrees, the normal operating range for the human ankle.

During controlled plantar flexion (CP), normal ankle function can be modeled as a linear rotational spring where ankle moment is proportional to ankle position. Thus, during the CP phase of walking, a linear torsional spring control can be used for the orthotic ankle joint. As a criterion for selecting a desired stiffness of the orthotic torsional spring, the controller can be used to analyze the ground reaction force generated at the moment of forefoot impact after each walking step. The extent of foot slap can be deemed too extreme, and the CP stiffness too low, if a high frequency force spike occurs at the moment of forefoot collision.

Figure 4B:
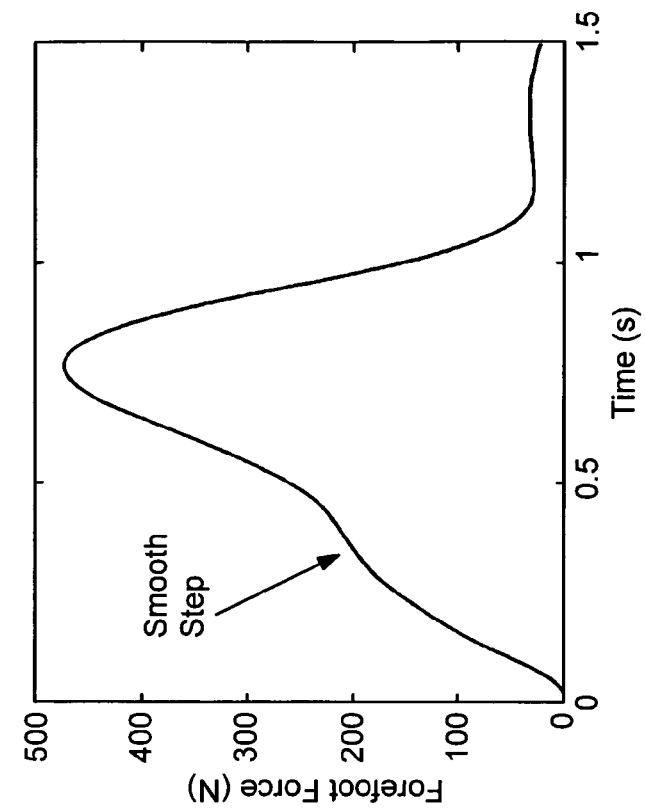
FIG. 4B is a representative forefoot ground reaction force from a normal participant.
Figure 4A:
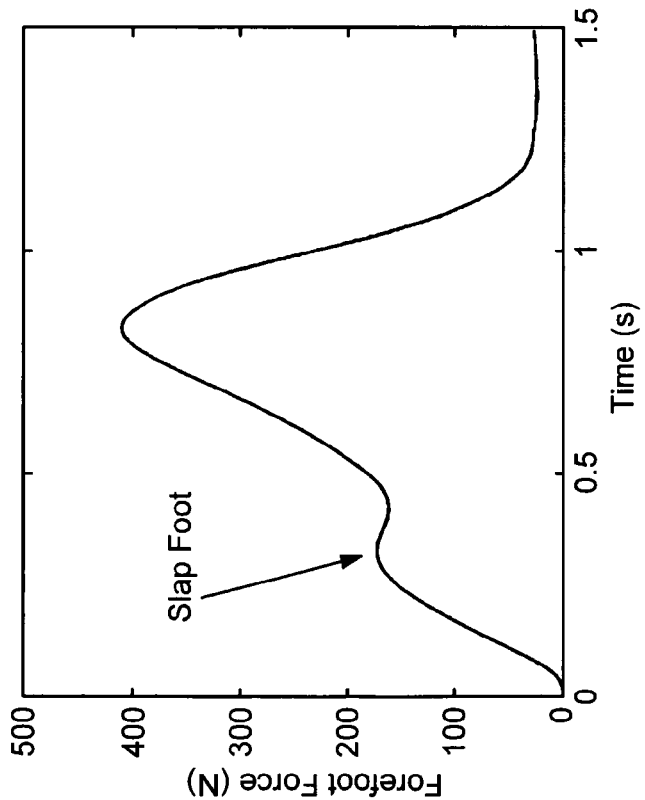
FIG. 4A is a representative forefoot ground reaction force from a drop foot participant.

In FIGS. 4A and 4B, a representative forefoot force signal from a drop foot participant is compared to a forefoot force signal from a normal participant. Both participants wore the AAFO 10 under a zero impedance control, and the forefoot force signal was computed from the sum of all four force transducer signals measured in the forefoot region. In FIG. 4A, a dual peak force pattern indicates the occurrence of foot slap in the drop foot participant, whereas in FIG. 4B, the lack of a dual force spike indicates that no foot slap had occurred in the normal participant.

To detect the dual peaks and the occurrence of foot slap, the AAFO controller can numerically differentiate the forefoot force and then filter that signal using a second order Butterworth filter with a cutoff frequency of about 0.6 Hz. If substantial foot slap occurs, the differential of the forefoot force is negative, and the stiffness of the orthotic torsional spring stiffness can be incremented. The CP stiffness can be started at zero and incremented by the rules shown in Table I, where the incremental stiffness ($\Delta\Gamma$) was 5.7 Nm/rad (0.1 Nm/deg), approximately 2% of the anticipated final ankle stiffness.

TABLE I

| Number of slaps in last 5 steps (n) | Change in Ankle Stiffness |
| --- | --- |
| 0 | $-\Delta\Gamma$ |
| 1 | 0 |
| 2–5 | $(n - 1) \Delta\Gamma$ |

Gait speed is an important step-to-step gait variation for which the AAFO 10 can respond and adapt. In a particular embodiment, the time of foot contact, defined as the time that a foot remains in contact with the ground from heel strike to toe-off, can be used as a measure of forward speed. With an expectation that orthotic CP stiffness should change with gait speed, the full range of gait contact times can be divided into bins, denoting velocity ranges. During each swing phase, stance time can be estimated from the orthotic force transducers 16, and the participant's time of contact bin, or forward speed range, can be selected. Within each bin, the AAFO controller can optimize the orthotic CP stiffness. In one embodiment, only three bins are necessary to span the full speed range of the participants.

Drop foot participants typically do not experience any difficulties during powered plantar flexion. Hence, the control objective of Contact 2 is to minimize orthotic joint impedance so as not to impede the participants' power plantar flexion movements. During this state, the SEA's 12 target force can be set to zero.

During the swing phase, a second-order, under-damped mechanical model (spring-damper PD control), previously used to characterize normal ankle function, can be used to control the orthotic ankle joint. Using the AAFO 10, each drop foot participant can walk at slow, self-selected, and fast speeds, and the swing phase ankle angle can be collected on both the affected and unaffected sides. At each speed, orthotic joint stiffness can be increased manually until the early swing phase dorsiflexion velocity measured on the affected side matched the unaffected side. Orthotic joint damping can be increased from zero until unwanted joint oscillations are removed. The final values of stiffness and damping in this particular embodiment are listed in Table II below.

TABLE II

| Gait Speed | K (Nm/rad) | B (Nms/rad) |
| --- | --- | --- |
| Slow | 28.65 | 0.57 |
| Normal | 37.24 | 1.03 |
| Fast | 45.84 | 1.15 |

The stiffness and damping values for the drop foot users are not correlated with gait speed directly, but with ranges of stance time, in the same manner to the CP stiffness control described earlier.

EXAMPLE

A clinical evaluation of the AAFO 10 was conducted in the Gait Laboratory at Spaulding Rehabilitation Hospital, Boston, Mass. Drop foot participants having only a unilateral drop foot condition were selected, and on their affected side, participants did not suffer from a gait disability other than drop foot. Both participants had an absence of strongly manifesting spasms and contractures in lower extremity joints. Finally, each participant had used an AFO for at least two years and therefore was experienced at AFO ambulation. Subjects reached a stable neurological state after the incident that caused their disability. Thus, no recovery of function was expected or found. Three normal subjects were matched for gender, height, weight, and age to the drop foot participants. Subject sex, age, mass, height, and self-selected gait speed are listed in Table III.

TABLE III

| Subject | Sex | Age (yr) | Mass (kg) | Height (m) | Self-Selected Gait Speed (m/s) |
| --- | --- | --- | --- | --- | --- |
| Drop Foot | M | 62 | 79.1 | 1.79 | 1.22 |
| Drop Foot | M | 62 | 95.4 | 1.77 | 1.07 |
| Normal | M | 66 | 76.6 | 1.70 | 1.39 |
| Normal | M | 67 | 86.1 | 1.75 | 1.01 |
| Normal | M | 67 | 73.2 | 1.70 | 1.22 |

Kinematic and kinetic data were measured on both the affected and unaffected sides using an eight-camera VICON 512 system and two AMTI force plates. The data were processed at 120 Hz with VICON Workstation using the standard model of the lower limbs included with the software. These data were then analyzed using MATLAB.

The subjects donned the AAFO in three different control conditions: zero, constant, and variable impedance. The zero impedance control setup was implemented by setting the target force on the SEA to zero, thereby minimizing the impedance contribution of the orthosis across the ankle joint. This setup was meant to approximate unassisted drop foot gait. For the constant impedance control setup, the AAFO controller commanded a constant joint stiffness, independent of walking phase and gait speed. This joint stiffness was the converged controlled plantar flexion (CP) stiffness from the variable impedance control that minimized the number of slap foot occurrences at the self-selected gait speed. This constant impedance control condition was designed to imitate conventional AFO technology employed in the treatment of drop foot gait.

For each controller, subjects walked at slow, self-selected, and fast gait speeds. The subjects first walked at their self-selected speed using the constant impedance control setup. The amount of time required to cover a specified distance was measured using a stopwatch. Subjects were then asked to reduce their time by 25% for the fast gait speed and increase their time by 25% for the slow gait speed. These times were then matched when testing the remaining two control conditions.

A stride cycle was defined as the period of time for two steps, and was measured from the initial heel contact of one foot to the next initial heel contact of the same foot. All data were time normalized to 100% of the stride cycle. The ankle angle data during a gait cycle were fitted with a cubic spline function and then resampled to 200 samples so that each point was 0.5% of the gait cycle.

In this study, it was assumed that normal gait was symmetrical and that deviations from a reference pattern were a sign of disability. To analyze spatial asymmetry, the step length on the affected side ($L_{affected}$) was subtracted from the step length on the unaffected side ($L_{unaffected}$) The difference in stride lengths ($L_{sym}$) should be zero for symmetric gait:

$$L_{sym} = L_{affected} - L_{unaffected} \quad (1)$$

To analyze temporal asymmetry, the step time on the affected side ($T_{affected}$) was subtracted from the step time on the unaffected side ($T_{unaffected}$). The difference in stride times ($T_{sym}$) should be zero for symmetric gait:

$$T_{sym} = T_{affected} - T_{unaffected} \quad (2)$$

A multiple comparison using a one-way analysis of variance (ANOVA) was used to determine which means were significantly different for the gait symmetry. P values less than 0.05 were considered significant for all tests.

Figure 5:
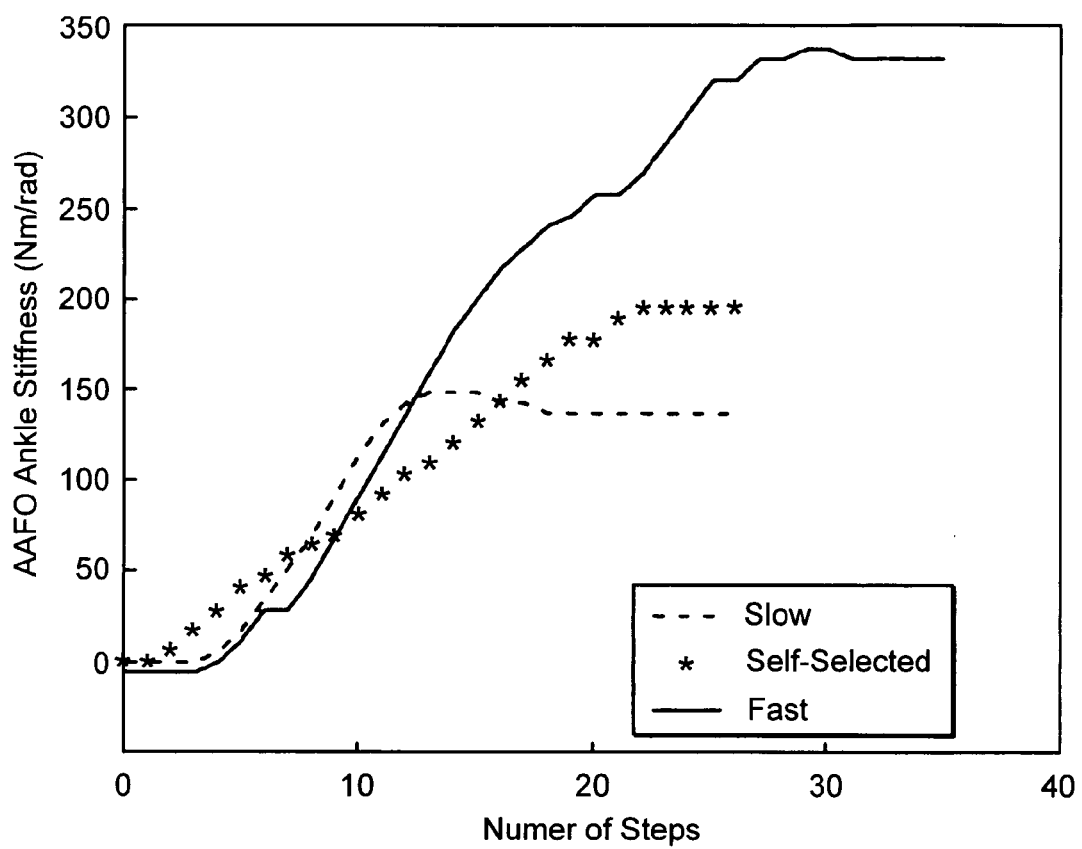
FIG. 5 illustrates orthotic joint stiffness plotted against the number of steps taken by a participant starting from an initial default impedance value of zero.

The first evaluation of the drop foot controller was to test whether the system was capable of converging to a final CP stiffness that reduced or prevented slap foot. For each of the three gait speeds, the controller was able to converge to a final stiffness value within 32 steps (FIG. 5). The CP stiffness increases with increasing gait speed. During the stiffness convergence at each of the three gait speeds, the occurrences of the high frequency forefoot force signal (typical of slap foot; see FIG. 4A) were reduced.

Figure 6:
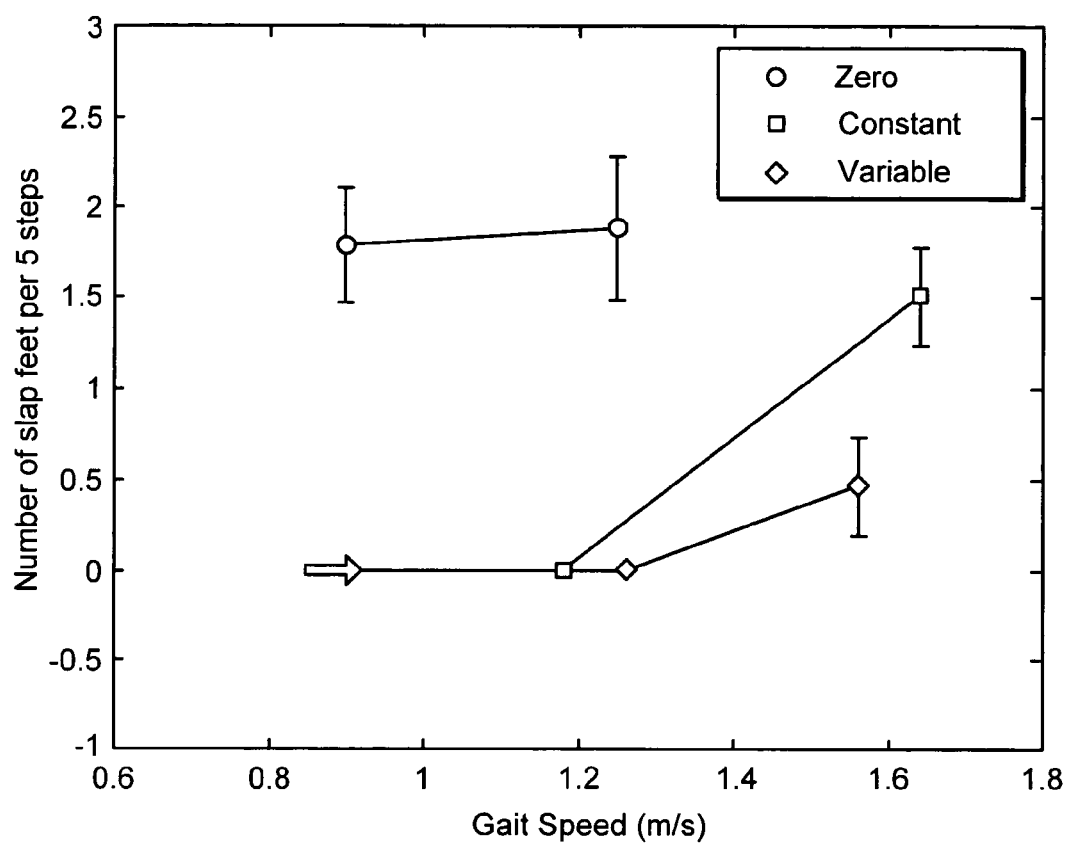
FIG. 6 illustrates slap foot occurrences per 5 steps (n=5) measured on two drop foot subjects walking at slow, self-selected, and fast speeds.

As a measure of the slap foot complication, the average number of occurrences of slap foot per 5 steps (25 steps total) were calculated for each drop foot subject, control condition, and gait speed (n=5). The participants were unable to walk at the fast gait speed using the zero force condition because it was not deemed safe. The constant impedance condition eliminated the occurrences of slap foot at the slow and self-selected gait speeds (FIG. 6). The three curves correspond to zero, constant, and variable impedance control conditions. However, slap foot occurrences increased at the fast gait speed. By adjusting CP stiffness with gait speed in the variable-impedance control condition, the number of occurrences of slap foot was reduced at the fast gait speed by 67% compared to the constant stiffness condition.

Figure 7:
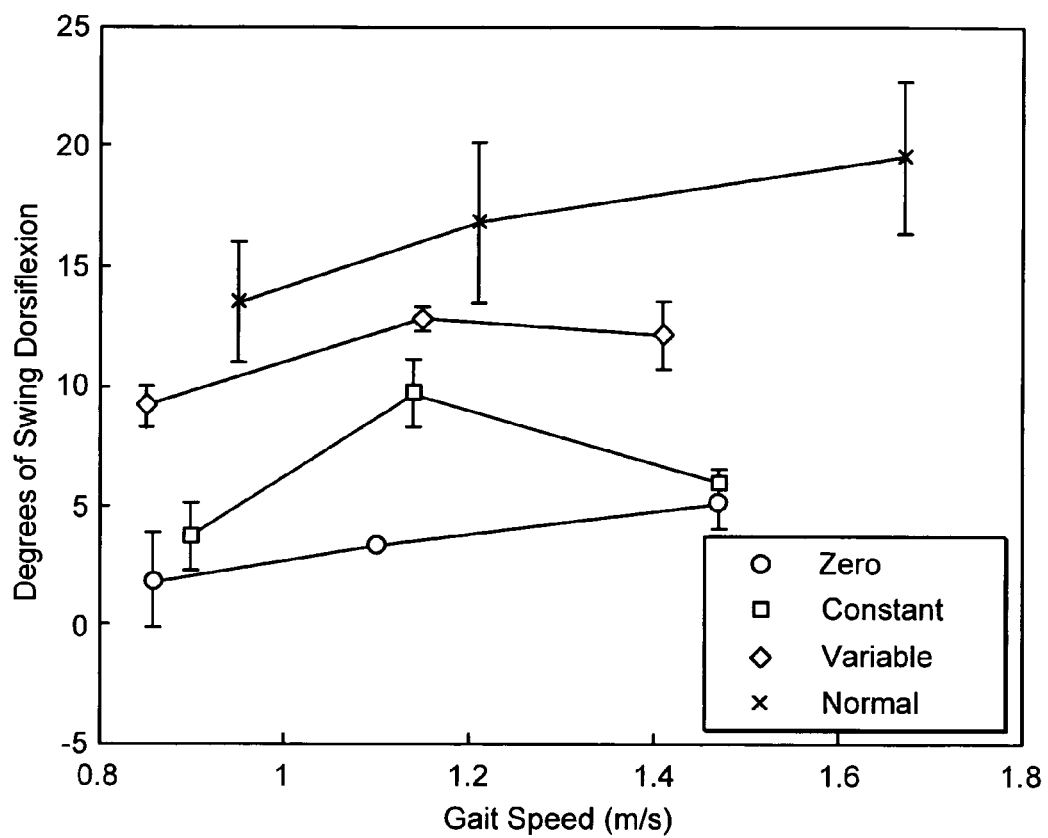
FIG. 7 is a plot of the amount of swing dorsiflexion for normal (n=3) and drop foot (n=2) participants.

To quantify the reduction of the second major complication of drop foot, or toe drag, the swing dorsiflexion angular range was used. The dorsiflexion angular range was defined as the maximum plantar flexion angle during the powered plantar flexion phase of stance minus the maximum dorsiflexion angle during swing. The variable impedance control was able to increase the amount of swing dorsiflexion as compared to the constant impedance condition by 200%, 37%, and 108% for slow, self-selected, and fast gait speeds, respectively (FIG. 7). All data points for the normal participants are an average of 15 trials, whereas for the drop foot participants the averages are over 20 trials.

Figure 8:
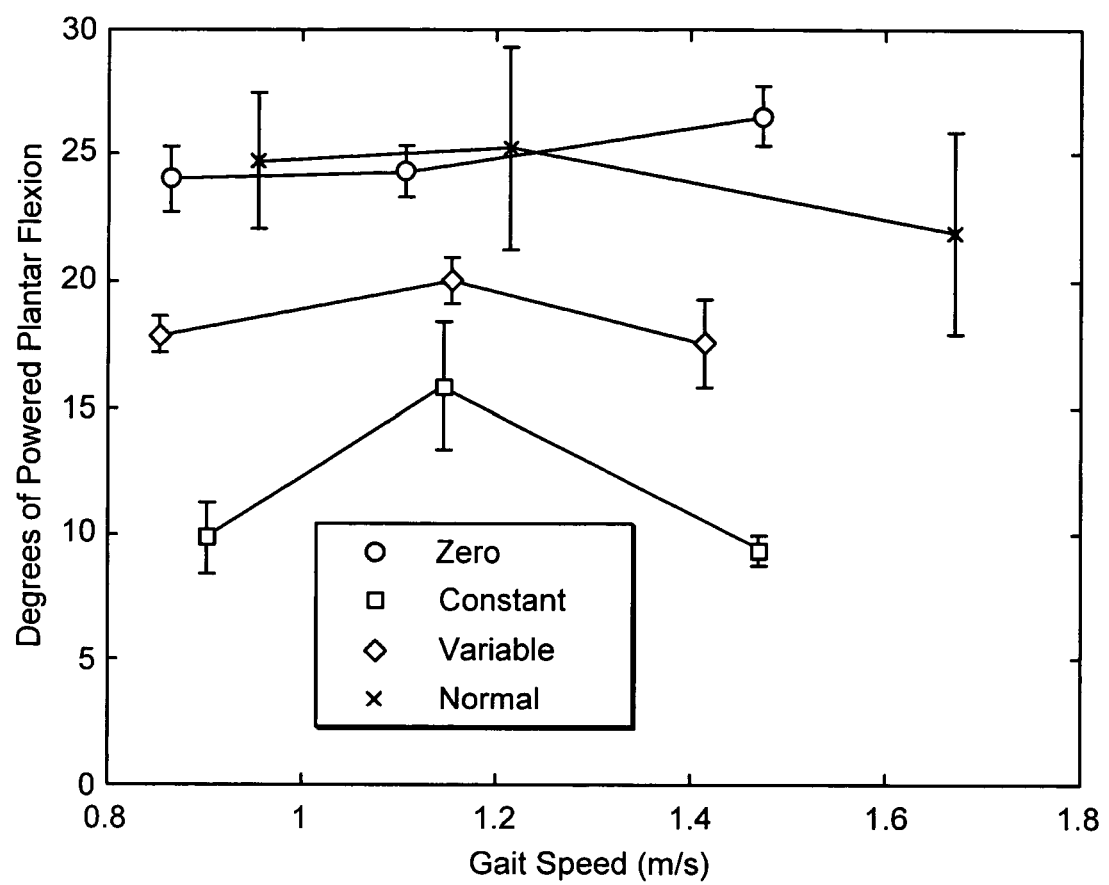
FIG. 8 illustrates the amount of powered plantar flexion for normal (n=3) and drop foot (n=2) participants.

A constant impedance ankle-foot orthosis hinders powered plantar flexion (PP) since a dorsiflexion moment will be exerted against the foot during late stance. As expected, the constant impedance condition reduced the PP angle as compared to the zero impedance condition and the normals (FIG. 8). Here the PP angle was defined as the maximum plantar flexion angle during power plantar flexion minus the maximum dorsiflexion angle during controlled dorsiflexion in stance. The variable-impedance controller had a larger PP angle than the constant impedance control condition by 89%, 25%, and 82% for the slow, self-selected, and fast gait speeds, respectively.

To evaluate spatial and temporal gait symmetry, the differences in step lengths ($L_{sym}$) (m) and step times ($T_{sym}$) (s) from the affected to the unaffected side were compared for each of the three control conditions (n=20). The results are set forth in Table IV below.

TABLE IV

| | $L_{sym}$(m) | | $T_{sym}$(s) | |
|---|---|---|---|---|
| | Self-selected | Slow | Self-selected | Slow |
| Zero Impedance | 0.08 ± 0.07 | 0.09 ± 0.09 | 0.09 ± 0.07 | 0.15 ± 0.16 |
| Constant Impedance | 0.04 ± 0.06 | 0.02 ± 0.08 | 0.07 ± 0.05 | 0.04 ± 0.12 |
| Variable Impedance | 0.02 ± 0.07 | 0.00 ± 0.07 | 0.02 ± 0.09 | 0.01 ± 0.16 |

Both $L_{sym}$ and $T_{sym}$ for the variable-impedance controller were significantly smaller than the zero impedance controller for both the self-selected and slow gait speeds (p<0.05). The zero and constant impedance conditions were significantly different for the slow gait speed (p<0.05). For the fast gait speed, a comparison was not possible because the step length for both sides could not be calculated for a single walking cycle.

An active ankle foot orthosis is provided in accordance with aspects of the present invention. Zero, constant, and variable-impedance control strategies were evaluated on two persons suffering from unilateral drop foot gait. It was found that actively adjusting joint impedance in response to walking phase and forward speed reduces the occurrence of slap foot, and provides for swing phase ankle kinematics more closely resembling normals as compared to the zero and constant impedance control schemes. Furthermore, it was found that a variable-impedance control allows for greater powered plantar flexion compared to a conventional constant stiffness approach where a dorsiflexion spring impedes powered plantar flexion movements during late stance.

Although the major complications of drop foot are reduced with a variable-impedance control, the findings do not support the hypothesis that changing orthotic joint impedance will result in a more symmetric gait between affected and unaffected legs in unilateral drop foot gait. To test the hypothesis, spatial and temporal gait symmetry was evaluated according to the difference in step lengths and times between affected and unaffected sides. When using the variable-impedance control, the difference in step time and step length was not significantly different from that measured with the constant impedance control condition. However, for both gait speeds analyzed, the variable-impedance controller did improve spatial and temporal gait symmetry compared to the zero impedance control condition, whereas the constant impedance control did not.

The CP stiffness was optimized within each gait speed range, or time of contact bin. After the variable-impedance controller adapted CP stiffness across gait speed, the final stiffness at the slow speed was 36% less, and at the fast speed, 57% greater than at the self-selected speed. Thus, from slow to fast speeds, stiffness increased more than two-fold. A constant stiffness spring tuned only to the self-selected speed allowed slap foot to occur at fast walking speeds (FIG. 6). It also made the ankle too stiff during slow walking, reducing the angular rotation of the ankle during controlled plantar flexion movements in early stance.

The primary concern for both the drop foot participants in the study was catching their toe during swing and losing their balance. With constant swing phase impedance, both users caught their toe at the fast gait speed. This was not surprising given the fact that, for normal gait, the amount of time to lift the foot and achieve toe clearance was found to decrease by a factor of two from slow to fast speeds. To achieve this time decrease with the AAFO 10, a four-fold increase in swing joint stiffness was necessary (Table II). Thus, changing orthotic joint impedance with gait speed, in order to lift the toe during swing, appears to be a desired control feature of the variable-impedance AAFO 10.

Normal ankle function has been modeled as a linear spring during controlled plantar flexion, and as a non-linear, stiffening spring during controlled dorsiflexion. Throughout the swing phase, the ankle has been represented by a linear torsional spring and damper. Given these differences in ankle function within a single gait cycle, an assistive ankle device, acting in parallel with the human ankle-foot complex, should ideally change its impedance in response to walking phase. To this end, a state controller was used in the AAFO 10, and joint impedance was modulated in response to walking phase.

During the controlled plantar flexion phase of walking, or Contact 1, a linear torsional spring control was employed where the stiffness was adjusted to prevent slap foot. From mid-stance to pre-swing, or the Contact 2 state, a zero impedance control was implemented so as not to impede normal powered plantar flexion movements. Finally, during the Swing state, a spring-damper PD control was implemented to provide toe clearance. The primary difficulty with the constant impedance control was the reduction of powered plantar flexion movements (FIG. 8). All data points for the normal participants are an average of 15 trials, whereas for the drop foot participants the average is over 20 trials. Here the spring-damper control used to prevent toe drag was acting against the foot when the users attempted to plantar flex their ankle during late stance.

The variable-impedance controller should have a similar maximum power plantarflexion angle as the zero impedance condition since both controllers were designed to not impede late stance power plantarflexion movements. However, this behavior was not observed (FIG. 8). It was discovered that the variable-impedance controller transitioned into the Swing state too early, before the foot actually left the ground, due to a lack of resolution in the forefoot force sensors. Consequently, the Swing spring-damper controller was activated too early, impeding power plantarflexion movements during late stance. In other embodiments, a foot switch can be positioned in the forefoot region to more accurately detect the event of toe-off.

In alternative embodiments, FES can be used to treat ankle foot gait pathologies, including drop foot gait. Instead of using a synthetic motor to vary ankle impedance, the muscles of the patient can be electrically stimulated to achieve desired ankle impedances as described herein. That is, a FES controller can be used to actively modulate ankle impedance to achieve a linear torsional spring during controlled plantar flexion to minimize forefoot collisions with the ground, minimize impedance during late stance, and achieve a spring-damper during a swing phase. Recent theoretical and experimental investigations have found that a positive force feedback FES control results in robust, spring-like muscle operations. Hence, for the stance phases of walking where a spring-like response is desired, a positive force feedback strategy can be employed. Here muscle or tendon force is the feedback sensory signal. The greater the force borne by the muscle-tendon unit, the greater is the muscle activation. This approach is not only robust to variations in muscle force-length and force-velocity curves, but is a control that rejects system energy disturbances as an emergent response.

While this invention has been particularly shown and described with references to various embodiments thereof including treatment of drop foot gait, it will be understood by those skilled in the art that various changes in form and details may be made therein without departing from the scope of the invention encompassed by the appended claims. For example, the devices and methods can be used to treat a variety of ankle foot gait pathologies, including patients suffering from anterior and/or posterior muscle weakness(es).

What is claimed is:

1. A variable-impedance active ankle foot orthosis comprising:
    a) an actuator configured to support a human ankle joint;
    b) at least one of an ankle angle sensor and a ground reaction force sensor; and
    c) a computer controller linked to the actuator and the sensor, the computer controller configured to receive sensory information from the at least one sensor and configured to modulate, in an updating manner, impedance of the actuator in response to at least one signal from the sensor, thereby modulating, by computer-controlled actuation, impedance of the human ankle joint, including a joint stiffness or damping of the ankle joint, from step-to-step of a walk cycle for treating an ankle foot gait pathology.

2. The device of claim 1, wherein the actuator includes a torsional spring control component that is configured to modulate impedance of the ankle joint.

3. The device of claim 1, wherein the actuator includes a spring-damper control component that is configured to modulate impedance of the ankle joint.

4. The device of claim 1, wherein the orthosis further includes a foot portion and wherein the actuator is coupled to the foot portion of the orthosis.

5. The device of claim 1, wherein the actuator is a series elastic actuator.

6. The device of claim 1, wherein the orthosis includes an ankle angle sensor.

7. The device of claim 1, wherein the orthosis includes one or more ground reaction force sensors.

8. The device of claim 1, wherein the orthosis includes an ankle angle sensor and one or more ground reaction force sensors.

9. The device of claim 4, wherein the orthosis further includes a foot switch at the foot portion that is connected to the computer controller.

10. The device of claim 1, wherein the controller is programmed to treat drop foot gait.

11. The device of claim 1, wherein the controller is programmed to treat a patient having anterior muscle weakness, posterior muscle weakness, or a combination thereof.

12. The device of claim 1, wherein the controller is programmed to minimize forefoot collisions from step-to-step of the walk cycle.

13. The device of claim 1, wherein the controller is programmed to minimize ankle joint stiffness or damping during a late stance portion of the step-to-step walk cycle.

14. The device of claim 1, wherein the controller is programmed to modulate ankle joint stiffness or damping of a spring-damper control during a swing phase portion of the step-to-step walk cycle.

15. The variable-impedance active ankle foot orthosis of claim 1, wherein the actuator includes a DC motor and a spring, wherein the DC motor is connected in series with the spring, whereby the actuator is configured to modulate the joint stiffness or damping of the ankle joint.

16. The variable-impedance active ankle foot orthosis of claim 15, further including a torsional spring control wherein the actuator is configured to modulate the joint stiffness of the ankle joint by controlling stiffness of the torsional spring control.

17. The variable-impedance active ankle foot orthosis of claim 16, further including a torsional spring-damper control, wherein the actuator is configured to modulate the damping of the ankle joint by controlling damping of the torsional spring-damper control.

18. A method comprising the step of modulating, by computer-controlled actuation, impedance, including joint stiffness or damping, of an ankle joint in an updating manner from step-to-step of a walk cycle, in response to at least one of an ankle angle sensor and a ground force reaction sensor, by modulating an actuator connected to the ankle joint.

19. The method of claim 18, wherein the step of modulating the joint stiffness or damping of the ankle joint during walking further includes modulating the ankle joint stiffness during controlled plantar flexion of the ankle joint, whereby forefoot collisions with the ground from step-to-step of the walk cycle are modulated.

20. The method of claim 19, wherein the stiffness of the ankle joint is modulated by modulating force applied to a spring that controls impedance of the ankle joint.

21. The method of claim 18, further comprising modulating the joint stiffness or damping during a late stance portion of the step-to step walk cycle.

22. The method of claim 18, wherein the step on modulating the joint stiffness or damping of the ankle joint during walking further comprising modulating ankle joint stiffness, or damping, or both of a torsional spring-damper control during a swing phase portion of a step-to-step walk cycle.

23. The method of claim 18, further including the steps of operatively coupling a spring to an orthosis, sensing at least one of ankle angle and ground reaction force during walking, and modulating the ankle joint impedance by controlling the spring in response to the ankle angle or ground reaction force.

24. The method of claim 18, wherein the modulation is in response to a ground reaction force sensor signal from the ground reaction force sensor during walking.

25. A method of treating an ankle foot gait pathology using functional electrical stimulation, comprising the step of:
applying computer-controlled electrical pulses in response to at least one of an ankle angle sensor and a ground force reaction sensor, to elicit muscle contraction of a human ankle joint to actively modulate impedance, including ankle stiffness, or damping, or both during walking, wherein joint stiffness or damping or both is modulated-in an updating manner from step-to-step of a walk cycle.

26. The method of claim 25, wherein the electrical pulses actively modulate stiffness of the ankle during a stance period.

27. The method of claim 25, wherein the electrical pulses actively modulate stiffness of the ankle joint.

28. The method of claim 25, wherein the electrical pulses actively modulate at least one of ankle joint stiffness or damping during a swing phase.

29. The method of claim 25, wherein the electrical pulses actively modulate at least one of ankle joint stiffness or damping of a spring damper control of the actuator during a swing phase of the walk cycle.

30. A variable-impedance active ankle foot orthosis, comprising:
a) an actuator that includes a spring, wherein the actuator is configured to support a human ankle joint;
b) at least one of an ankle angle sensor and ground reaction force sensor; and
c) a computer controller linked to the actuator and the sensor, the actuator configured to receive sensory information from the at least one sensor and to modulate impedance, including a joint stiffness or damping of an ankle joint, by controlling compression of the spring in response to the sensory information comprising at least one of an ankle angle and a ground reaction force, the actuator modulating the joint stiffness or damping of the ankle joint by controlling the spring in an updating manner from step-to-step of a walk cycle in response to the at least one of ankle angle and ground reaction force.

31. A method of treating an ankle foot gait pathology using functional electrical stimulation, comprising the step of:
applying computer-controlled electrical pulses, in response to at least one of an ankle angle sensor and a ground force reaction sensor, to elicit muscle contractions of a human ankle joint to actively modulate impedance, including ankle stiffness, or, damping, or both in an updating manner from step-to-step of a walking cycle, the joint stiffness or damping further being modulated by controlling a spring connected to an orthosis supporting the human ankle joint.

32. A variable impedance active ankle foot orthosis comprising:
a) an actuator configured to support a human ankle joint;
b) at least one of a ground reaction force sensor and an ankle angle sensor; and
c) a computer controller linked to the actuator and to the sensor,
wherein the orthosis is configured to receive sensory information from the at least one sensor and configured to modulate, by computer-controlled actuation, ankle joint impedance, including a joint stiffness or damping of an ankle joint, wherein modulation of the joint impedance is adaptive in nature.

33. A device for treating an ankle foot gait pathology comprising:
an orthosis including an orthosis leg portion configured to be attachable to a leg of a person and an orthosis foot portion configured to be attachable to a foot of the person; and
an actuator configured to act on a spring;
at least one of an ankle angle sensor and a ground reaction force sensor; and
a computer controller linked to the actuator and the sensor, the computer controller configured to receive sensory information from the at least one sensor and configured to modulate by computer-controlled actuation, impedance, including joint stiffness or damping of the ankle joint, wherein modulation of joint impedance is adaptive in nature.

34. A method comprising modulating, by computer-controlled actuation, impedance, including joint stiffness or damping of an ankle joint wherein modulation of joint impedance is adaptive in nature and in response to at least one of an ankle angle sensor and a ground force reaction sensor, and wherein the actuator is an actuator that is connected to an orthosis that supports an ankle joint.

35. A variable impedance active ankle foot orthosis comprising:
   a) an actuator and a spring operatively linked to the actuator
   b) an ankle angle sensor;
   c) a ground force reaction sensor; and
   d) a controller linked to the sensors and to the actuator, wherein the actuator is configured to receive sensory information from the at least two sensors and configured to modulate, by computer-controlled actuation, impedance, including a joint stiffness or damping of an ankle joint, by controlling compression of the spring, in response to the two sensors during walking, the actuator modulating the joint stiffness or damping of the ankle joint, wherein modulation of joint impedance is adaptive in nature.

36. A method of treating an ankle foot gait pathology using functional electrical stimulation, comprising the steps of:
   applying electrical pulses to elicit muscle contractions to actively modulate, by computer-controlled actuation, impedance, including ankle joint stiffness or damping, or both, of an ankle joint, wherein modulation of joint impedance is adaptive in nature, the modulation being in response to at least one of an ankle angle sensor or a ground reaction force sensor,
   the joint stiffness or damping further being modulated by controlling a spring linked to an orthosis that is supporting the ankle joint.

* * * * *